United States Patent
Hamamoto et al.

(10) Patent No.: US 10,675,593 B2
(45) Date of Patent: Jun. 9, 2020

(54) VIRUS REMOVAL MEMBRANE

(71) Applicant: ASAHI KASEI MEDICAL CO., LTD., Tokyo (JP)

(72) Inventors: Ryo Hamamoto, Tokyo (JP); Tomoko Hongo, Tokyo (JP); Yusuke Kon, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 15/302,278

(22) PCT Filed: Apr. 10, 2015

(86) PCT No.: PCT/JP2015/061286
§ 371 (c)(1),
(2) Date: Oct. 6, 2016

(87) PCT Pub. No.: WO2015/156401
PCT Pub. Date: Oct. 15, 2015

(65) Prior Publication Data
US 2017/0028360 A1    Feb. 2, 2017

(30) Foreign Application Priority Data
Apr. 11, 2014  (JP) ................................. 2014-082368

(51) Int. Cl.
*B01D 71/10* (2006.01)
*B01D 69/06* (2006.01)
(Continued)

(52) U.S. Cl.
CPC ............. *B01D 71/10* (2013.01); *B01D 65/10* (2013.01); *B01D 67/0011* (2013.01);
(Continued)

(58) Field of Classification Search
None
See application file for complete search history.

(56) References Cited

U.S. PATENT DOCUMENTS

| | | |
|---|---|---|
| 4,808,315 A | 2/1989 | Manabe et al. |
| 4,816,072 A | 3/1989 | Harley et al. |

(Continued)

FOREIGN PATENT DOCUMENTS

| | | |
|---|---|---|
| EP | 1563895 | 8/2005 |
| JP | 63-088007 | 4/1988 |

(Continued)

OTHER PUBLICATIONS

Search Report issued in European Patent Office (EPO) Patent Application No. 15777331.8, dated Apr. 4, 2017.
(Continued)

*Primary Examiner* — Krishnan S Menon
(74) *Attorney, Agent, or Firm* — Greenblum & Bernstein, P.L.C.

(57) ABSTRACT

A virus removal membrane is formed from cellulose, in which, when a solution containing gold colloids having a diameter of 20 nm is applied through a primary surface to the virus removal membrane to allow the virus removal membrane to capture the gold colloids for measurement of brightness in a cross section of the virus removal membrane, a value obtained by dividing a standard deviation of a value of an area of a spectrum of variation in the brightness by an average of the value of the area is 0.01 or more and 1.5 or less; and a thickness of a portion, where gold colloids having a diameter of 20 nm or more and 30 nm or less are captured, in the cross section of the virus removal membrane in a wet state is 10.0 μm or more and 30.0 μm or less.

13 Claims, 8 Drawing Sheets

(51) Int. Cl.
    *B01D 69/02*     (2006.01)
    *B01D 67/00*     (2006.01)
    *B01D 69/08*     (2006.01)
    *B01D 65/10*     (2006.01)
    *C07K 1/34*     (2006.01)
    *G01J 1/44*     (2006.01)

(52) U.S. Cl.
    CPC ......... *B01D 67/0013* (2013.01); *B01D 69/02* (2013.01); *B01D 69/06* (2013.01); *B01D 69/08* (2013.01); *B01D 69/087* (2013.01); *C07K 1/34* (2013.01); *G01J 1/44* (2013.01); *B01D 2325/02* (2013.01); *B01D 2325/022* (2013.01); *B01D 2325/023* (2013.01); *B01D 2325/04* (2013.01); *B01D 2325/20* (2013.01); *G01J 2001/444* (2013.01)

(56) References Cited

U.S. PATENT DOCUMENTS

| | | | |
|---|---|---|---|
| 5,236,588 | A | 8/1993 | Zhang et al. |
| 6,797,169 | B1 | 9/2004 | Ide et al. |
| 2006/0016748 | A1 | 1/2006 | Koguma et al. |
| 2009/0145831 | A1* | 6/2009 | Manabe ............... B01D 63/082 210/232 |
| 2010/0096328 | A1* | 4/2010 | Hamasaki ............ B01D 65/102 210/638 |

FOREIGN PATENT DOCUMENTS

| | | |
|---|---|---|
| JP | 1-148305 | 6/1989 |
| JP | 4-371221 | 12/1992 |
| JP | 05-000233 | 1/1993 |
| JP | 2003-275300 | 9/2003 |
| JP | 2008-272636 | 11/2008 |
| JP | 2010-14564 | 1/2010 |
| JP | 2011-136305 | 7/2011 |
| JP | 2012-91154 | 5/2012 |
| JP | 2012-206063 | 10/2012 |
| JP | 2013/012024 | 1/2013 |
| JP | 2013-71100 | 4/2013 |
| WO | 01/14047 | 3/2001 |
| WO | 2004/035180 | 4/2004 |
| WO | 2009/060836 | 5/2009 |

OTHER PUBLICATIONS

Search Report issued in Japan Patent Application No. PCT/JP2015/061286, dated Jun. 9, 2015.
International Preliminary Report on Patentability in Japan Patent Application No. PCT/JP2015/061286, dated Oct. 12, 2016.
English Translation of the Written Opinion of the International Searching Authority, dated Jun. 9, 2015.

* cited by examiner

VIRUS CAPTURE PORTION

Fig. 5

| Manufacturing Conditions | | | Example 1 | Example 2 | Example 3 | Example 4 | Example 5 | Example 6 | Example 7 | Example 8 | Example 9 |
|---|---|---|---|---|---|---|---|---|---|---|---|
| Cellulose Concentrations | | wt% | 7.58 | 7.58 | 7.58 | 7.58 | 7.55 | 7.52 | 7.52 | 7.52 | 7.55 |
| Average Molecular Weight | | | $1.44 \times 10^5$ | $1.44 \times 10^5$ | $1.44 \times 10^5$ | $1.44 \times 10^5$ | $1.44 \times 10^5$ | $1.44 \times 10^5$ | $1.44 \times 10^5$ | $1.44 \times 10^5$ | $1.44 \times 10^5$ |
| Addition of Sodium Sulfate | | wt% | 0.05 | 0.25 | 0.5 | 0.5 | 0.5 | 0.5 | 0.05 | 0.5 | 0.25 |
| Composition of External Coagulation Liquid | Acetone | wt% | 37.5 | 37.5 | 37.5 | 37.5 | 28 | 30 | 28 | 30 | 28 |
| | Ammonia | wt% | 0.1 | 0.1 | 0.1 | 0.1 | 0 | 0 | 0 | 0 | 0 |
| Composition of Internal Coagulation Liquid | Acetone | wt% | 45 | 45 | 45 | 45 | 38 | 38 | 38 | 38 | 38 |
| | Ammonia | wt% | 0.65 | 0.65 | 0.65 | 0.65 | 0.65 | 0.65 | 0.65 | 0.65 | 0.65 |
| Amount of Discharged Raw Spinning Solution | | cc/min | 3.00 | 3.00 | 3.00 | 3.00 | 3.65 | 3.65 | 3.65 | 3.65 | 3.65 |
| Amount of Discharged Internal Coagulation Liquid | | cc/min | 1.8 | 1.8 | 1.8 | 1.8 | 1.8 | 1.8 | 1.8 | 1.8 | 1.8 |
| Diameter of Funnel Narrow Tube | | mm | 7 | 7 | 7 | 7 | 7 | 7 | 7 | 7 | 7 |
| Flow Rate of External Coagulation Liquid | | cc/min | 140 | 160 | 180 | 200 | 140 | 140 | 140 | 180 | 160 |
| Average Flow Velocity of External Coagulation Liquid in Funnel | | m/min | 3.6 | 4.2 | 4.7 | 5.2 | 3.6 | 3.6 | 3.6 | 4.7 | 4.2 |
| Spinning Speed | | m/min | 10 | 10 | 10 | 10 | 10 | 10 | 10 | 10 | 10 |
| Average Flow Velocity of External Coagulation Liquid/Spinning Speed | | | 0.36 | 0.42 | 0.47 | 0.52 | 0.36 | 0.36 | 0.36 | 0.47 | 0.42 |
| Spinning Temperature | | °C | 26 | 26 | 26 | 26 | 28.5 | 28.5 | 28.5 | 28.5 | 28.5 |
| Inner Diameter | | μm | 335.8 | 332.4 | 332.7 | 332.7 | 377.5 | 383.7 | 391.4 | 379.4 | 395.2 |
| Thickness | | μm | 26.6 | 25.7 | 26.8 | 26.8 | 36.8 | 37.6 | 39.2 | 35.9 | 34.8 |
| Average Pore Size | | nm | 14.2 | 14.1 | 14.0 | 14.0 | 18.3 | 19.6 | 18.1 | 18.3 | 17.5 |
| Bubble Point | | MPa | 1.6 | 1.6 | 1.6 | 1.6 | 1.4 | 1.2 | 1.4 | 1.4 | 1.5 |
| Pure Water Permeation Rate (Before Sterilization) | | L/m²/hrs/0.1MPa | 58.8 | 56.1 | 56.1 | 56.1 | 89.1 | 101.7 | 86.4 | 88.9 | 84.7 |

Fig. 6

| | | | Comparative Example 1 | Comparative Example 2 | Comparative Example 3 | Comparative Example 4 | Comparative Example 5 |
|---|---|---|---|---|---|---|---|
| Manufacturing Conditions | Cellulose Concentrations | wt% | 7.58 | 7.58 | 7.58 | 7.58 | 7.58 |
| | Average Molecular Weight | | $1.44 \times 10^5$ | $1.44 \times 10^5$ | $1.44 \times 10^5$ | $1.44 \times 10^6$ | $1.44 \times 10^5$ |
| | Addition of Sodium Sulfate | wt% | 0 | 0.01 | 1 | 0.5 | 0.5 |
| | Composition of External Coagulation Liquid | Acetone wt% | 37.5 | 37.5 | 37.5 | 37.5 | 37.5 |
| | | Ammonia wt% | 0.1 | 0.1 | 0.1 | 0.1 | 0.1 |
| | Composition of Internal Coagulation Liquid | Acetone wt% | 45 | 45 | 45 | 45 | 45 |
| | | Ammonia wt% | 0.65 | 0.65 | 0.65 | 0.65 | 0.65 |
| | Amount of Discharged Raw Spinning Solution | cc/min | 3 | 3 | 3 | 3 | 3 |
| | Amount of Discharged Internal Coagulation Liquid | cc/min | 1.8 | 1.8 | 1.8 | 1.8 | 1.8 |
| | Diameter of Funnel Narrow Tube | mm | 7 | 7 | 7 | 7 | 7 |
| | Flow Rate of External Coagulation Liquid | cc/min | 180 | 180 | 180 | 120 | 210 |
| | Average Flow Velocity of External Coagulation Liquid in Funnel | m/min | 4.7 | 4.7 | 4.7 | 3.1 | 5.5 |
| | Spinning Speed | m/min | 10 | 10 | 10 | 10 | 10 |
| | Average Flow Velocity of External Coagulation Liquid/Spinning Speed | | 0.47 | 0.47 | 0.47 | 0.31 | 0.55 |
| | Spinning Temperature | °C | 26 | 26 | 26 | 26 | 26 |
| | Inner Diameter | μm | 334.8 | 334.8 | — | 334.8 | — |
| | Thickness | μm | 26.5 | 26.5 | — | 26.5 | — |
| | Average Pore Size | nm | 14.2 | 14.2 | — | 14.2 | — |
| | Bubble Point | MPa | 1.6 | 1.6 | — | 1.6 | — |
| | Pure Water Permeation Rate (Before Sterilization) | L/m²/hrs/0.1MPa | 59.8 | 59.8 | — | 59.8 | — |

Fig. 7

|  |  |  | | Example 1 | Example 2 | Example 3 | Example 4 | Example 5 | Example 6 | Example 7 | Example 8 | Example 9 |
|---|---|---|---|---|---|---|---|---|---|---|---|---|
| Evaluations | Variation Coefficient of Amount of Captured Gold Colloids | | | 1.40 | 1.10 | 0.85 | 0.58 | 0.21 | 0.63 | 1.30 | 0.47 | 0.90 |
| | Thickness of Dense Layer | | μm | 14.7 | 15.6 | 16.0 | 16.0 | 15.3 | 14.9 | 14.1 | 20.0 | 17.3 |
| | First Attainment Level, Second Attainment Level | 30 nm | % | 25~46 | 23~37 | 23~44 | 23~44 | 24~32 | 25~34 | 27~38 | 20~32 | 23~36 |
| | | 20 nm | % | 47~70 | 32~72 | 42~74 | 42~74 | 36~58 | 35~58 | 40~55 | 41~64 | 38~61 |
| | | 15 nm | % | 75~84 | 70~81 | 77~86 | 77~86 | 60~74 | 60~75 | 60~73 | 68~80 | 61~77 |
| | Logarithmic Removal Rate of Gold Colloids | 30 nm | LRV | ≧1.40 | ≧1.40 | ≧1.40 | ≧1.40 | ≧1.40 | ≧1.40 | ≧1.40 | ≧1.40 | ≧1.40 |
| | | 20 nm | LRV | ≧1.40 | ≧1.40 | ≧1.40 | ≧1.40 | ≧1.40 | ≧1.40 | ≧1.40 | ≧1.40 | ≧1.40 |
| | | 15 nm | LRV | 0.41 | 0.31 | 0.31 | 0.31 | 0.26 | 0.20 | 0.20 | 0.26 | 0.24 |
| | | 10 nm | LRV | 0.08 | 0.08 | 0.08 | 0.08 | 0.04 | 0.04 | 0.03 | 0.04 | 0.03 |
| Effect | PPV-LRV | | | 4.50 | 5.00 | ≧6.00 | ≧6.00 | 5.30 | 5.00 | 4.50 | ≧6.00 | 5.50 |

Fig. 8

| | | | Comparative Example 1 | Comparative Example 2 | Comparative Example 3 | Comparative Example 4 | Comparative Example 5 |
|---|---|---|---|---|---|---|---|
| | Variation Coefficient of Amount of Captured Gold Colloids | | 1.70 | 1.60 | (Could Not Be Produced) | 1.60 | (Could Not Be Produced) |
| | Thickness of Dense Layer | $\mu m$ | 9.0 | 9.0 | — | 9.0 | — |
| | First Attainment Level, Second Attainment Level | 30 nm | 30~37 | 30~37 | — | 30~37 | — |
| | | 20 nm | 37~60 | 37~60 | — | 37~60 | — |
| Evaluations | | 15 nm | 70~82 | 70~82 | — | 70~82 | — |
| | Logarithmic Removal Rate of Gold Colloids | 30 nm | 1.40 | 1.40 | — | 1.40 | — |
| | | 20 nm | 1.30 | 1.30 | — | 1.30 | — |
| | | 15 nm | 0.25 | 0.25 | — | 0.25 | — |
| | | 10 nm | 0.08 | 0.08 | — | 0.08 | — |
| Effect | PPV-LRV | | 3.50 | 3.50 | — | 3.50 | — |

VIRUS REMOVAL MEMBRANE

TECHNICAL FIELD

The present invention relates to a virus removal membrane for removing viruses from a solution.

BACKGROUND ART

In recent years, a measure to enhance virus safety has been necessary for not only plasma derivatives derived from human blood, but also bio-pharmaceuticals. Therefore, pharmaceutical manufacturers have studied to introduce a virus removal/inactivation step in a manufacturing process. In particular, a virus removal method by filtration with a virus removal membrane is an effective method that can provide virus reduction without denaturing a useful protein.

Among viruses, in particular, parvovirus has been reported with respect to a case of infection with human parvovirus B19 in the field of plasma derivatives, and a case of contamination of CHO (Chinese Hamster Ovary) cells with mouse parvovirus in the bio-pharmaceutical field. Parvovirus, which is a small virus, has no envelope, and it is thus physicochemically stable and is resistant to heating, a low pH and a treatment with a chemical agent which correspond to an inactivation step generally performed during a pharmaceutical manufacturing process. Therefore, there is a growing need for parvovirus removal by a virus removal membrane, as a virus removal method having a different mechanism from that of an inactivation method.

For example, Patent Literature 1 discloses a polymer porous hollow fiber membrane having a pore structure in which the in-plane porosity is first decreased from the inner wall surface of the membrane towards the wall inside thereof, then takes at least one local minimum value, and is thereafter increased at the outer wall portion thereof (hereinafter, also referred to as "gradient structure"), as well as a virus removal method including filtering an aqueous protein solution by use of the membrane. The virus removal membrane having such a gradient structure and having a specific average pore size is considered to be suitable for virus removal at a high removal rate and protein recovery at a high permeation efficiency without denaturing a protein, in virus removal from an aqueous protein solution. The virus removal membrane exhibits removal property of viruses having a medium size (35 nm to 55 nm), but it can ensure no virus removal property of small viruses (parvovirus and the like).

Patent Literature 2 discloses a method of producing a hollow fiber membrane that can achieve a high virus removal property, and this method involves coagulation of a cuprammonium cellulose solution in a U-tube to suppress, as much as possible, of structural disorder due to stretching during structure formation of microphase separation. The method is effective for removal of viruses having a medium size (JEV), but it can ensure no sufficient removal property of small viruses.

Patent Literature 3 discloses removal of a parvovirus as a small virus by adjustment of the ratio (BP/γ) of the bubble point BP (MPa) to the surface tension γ (N/m) of a virus removal membrane.

Patent Literature 4 discloses characteristic evaluation of a virus removal membrane, which is performed using viruses and proteins. This Literature describes staining viruses and proteins by a fluorescent dye, and a membrane structure necessary for high virus removal performance and protein permeability. No sufficient studies, however, have been made about conditions for ensuring virus removal property, and no studies have been made for enhancements in filtration efficiencies (filtration throughput and filtration rate).

CITATION LIST

Patent Literature

Patent Literature 1: Japanese Patent Laid-Open No. 1-148305
Patent Literature 2: Japanese Patent Laid-Open No. 4-371221
Patent Literature 3: International Publication No. WO 01/14047
Patent Literature 4: Japanese Patent Laid-Open No. 2010-14564

SUMMARY OF INVENTION

Technical Problem

A virus removal membrane having high virus removal properties with respect to small viruses (for example, parvovirus) having a size close to the size of a useful protein and also having high protein filtration efficiency has been demanded in the pharmaceutical manufacturing site, and the demand for a virus removal membrane has been increasingly severe year by year.

In view of the above, the total amount of viruses to be loaded to a virus removal membrane (the amount of viruses to be spiked to a pharmaceutical protein, or the total amount thereof to be filtered off) has been increased in a virus removal membrane evaluation test in which the capacity of a virus removal step in a pharmaceutical manufacturing process is examined. Thus, conditions for passing the virus removal membrane evaluation test have been increasingly severe year by year.

It has, however, been conventionally difficult to maintain high filtration efficiency while maintaining high virus removal performance. One object of the present invention is then to provide a virus removal membrane having high virus removal property and filtration efficiency.

Solution to Problem

An aspect of the present invention provides a virus removal membrane for removing viruses from a protein-containing solution, the virus removal membrane including a primary surface to which the protein-containing solution is applied, and a secondary surface from which a liquid that permeates through the virus removal membrane is flowed, wherein, when a solution containing gold colloids having a diameter of 20 nm is applied through the primary surface to the virus removal membrane to allow the virus removal membrane to capture the gold colloids for measurement of brightness in a cross section of the virus removal membrane, a value obtained by dividing a standard deviation of a value of an area of a spectrum of variation in the brightness by an average of the value of the area of the spectrum of variation in the brightness is 0.01 or more and 1.50 or less; a thickness of a portion where gold colloids having a diameter of 20 nm or more and 30 nm or less are captured in the cross section of the virus removal membrane in a wet state is 10.0 μm or more and 30.0 μm or less; and the virus removal membrane is formed of cellulose.

For example, a portion where gold colloids having a diameter of 30 nm are captured is located at a place corresponding to 15% or more and 60% or less of a thickness of the virus removal membrane from the primary surface, a portion where gold colloids having a diameter of 20 nm are captured is located at a place corresponding to 25% or more and 85% or less of the membrane thickness from the primary surface, and a portion where gold colloids having a diameter of 15 nm are captured is located at a place corresponding to 60% or more and 90% or less of the membrane thickness from the primary surface, in the cross section of the virus removal membrane in a wet state.

For example, the virus removal membrane does not capture gold colloids having a diameter of 10 nm. In addition, for example, in the virus removal membrane, a logarithmic removal rate of gold colloid having a diameter of 30 nm is 1.00 or more, a logarithmic removal rate of gold colloid having a diameter of 20 nm is 1.00 or more, a logarithmic removal rate of gold colloid having a diameter of 15 nm is 0.10 or more, and a logarithmic removal rate of gold colloid having a diameter of 10 nm is less than 0.10. For example, in the virus removal membrane, an average pore size is 13 nm or more and 21 nm or less. For example, a pore size is decreased and then increased, from the primary surface towards the secondary surface in the cross section of the virus removal membrane. For example, the portion where gold colloids are captured in the virus removal membrane encompasses a portion where the pore size is a minimum value.

For example, a thickness of the virus removal membrane is 24 μm or more and 41 μm or less in a dry state. In addition, for example, a bubble point of the virus removal membrane is 1.2 MPa or more and 1.8 MPa or less, and a pure water permeation rate is 30 L/m$^2$/hrs/0.1 MPa, or more and 120 L/m$^2$/hrs/0.1 MPa, or less. The virus removal membrane may be a hollow fiber membrane or a flat membrane.

For example, the value obtained by dividing a standard deviation of an area value of a spectrum of variation in the brightness by an average of an area value of a spectrum of variation in the brightness may be 0.01 or more and 1.20 or less. For example, the thickness of a portion where gold colloids having a diameter of 20 nm or more and 30 nm or less are captured in the cross section of the virus removal membrane in a wet state may be 13.0 μm or more and 20.0 μm or less.

Advantageous Effects of Invention

The present invention makes it possible to provide a virus removal membrane having high virus removal property and filtration efficiency.

BRIEF DESCRIPTION OF DRAWINGS

FIG. 5 is a table showing manufacturing conditions of a virus removal membrane according to each Example of the present invention.

FIG. 6 is a table showing manufacturing conditions of a virus removal membrane according to each Comparative Example of the present invention.

FIG. 7 is a table showing evaluation results of a virus removal membrane according to each Example of the present invention.

FIG. 8 is a table showing evaluation results of a virus removal membrane according to each Comparative Example of the present invention.

DESCRIPTION OF EMBODIMENTS

Hereinafter, embodiments of the present invention are described. In the following description of drawings, the same or similar part is represented by the same or similar reference sign. The drawings, however, are schematic, and are not accurately illustrated by specific dimensions and the like. Accordingly, specific dimensions and the like are required to be understood in view of the following description, and any part whose dimension relationship and ratio are different among the drawings is, of course, included.

Figure 1:
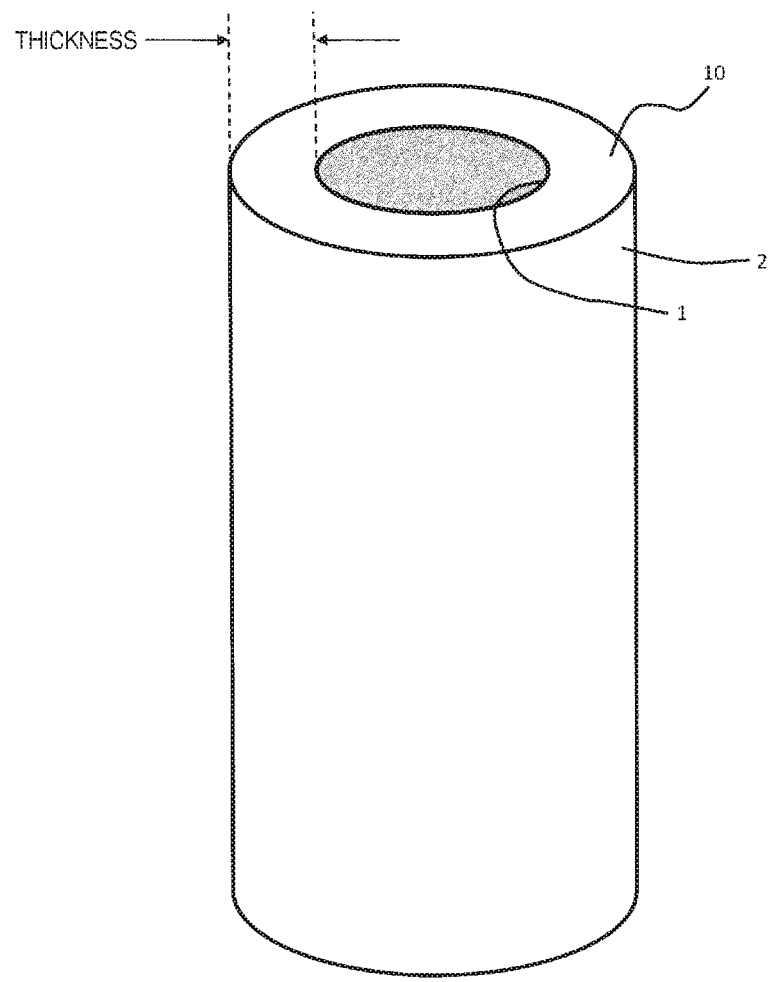
FIG. 1 is a schematic view of a virus removal membrane having a hollow fiber membrane shape, according to an embodiment of the present invention.

As illustrated in FIG. 1, a virus removal membrane 10 for removing viruses from a protein-containing solution, according to an embodiment, includes a primary surface 1 to which the protein-containing solution is applied, and a secondary surface 2 from which a liquid that permeates through the virus removal membrane 10 is flowed.

Figure 2:
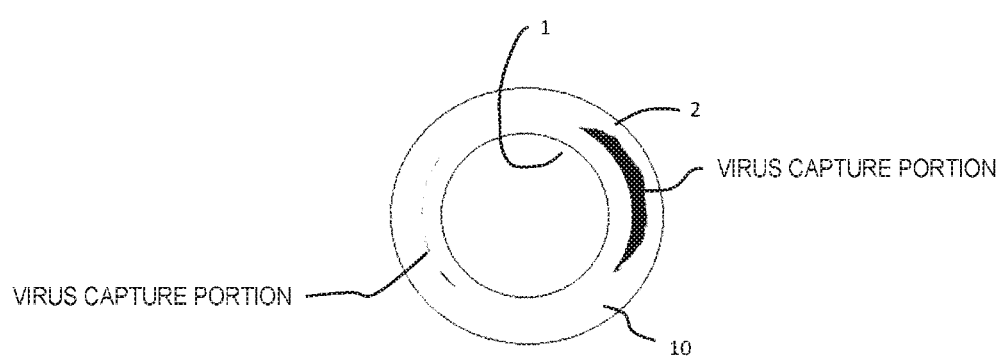
FIG. 2 is a schematic view of a virus capture portion in a virus removal membrane having a hollow fiber membrane shape, according to Reference Example of the present invention.
Figure 3:
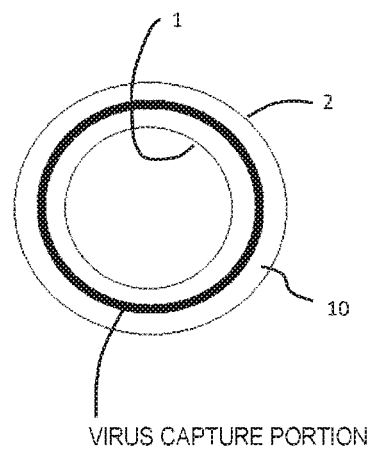
FIG. 3 is a schematic view of a virus capture portion in a virus removal membrane having a hollow fiber membrane shape, according to an embodiment of the present invention.

Small viruses to be removed by the virus removal membrane 10 have a diameter of, for example, 10 to 30 nm, or 18 to 24 nm. Specific examples of the viruses include parvovirus. Parvovirus has a diameter of about 20 nm. The virus removal membrane 10 has a virus capture portion, where viruses are captured, in the cross section thereof. In the virus removal membrane 10, the amount of viruses captured on the virus capture portion in the cross section is preferably uniform regardless of a point on a filtration surface (primary surface 1) which the solution enters. The reason for this is because, if the amount of viruses captured in the virus removal membrane 10 is not uniform depending on a point on the filtration surface, the solution is concentrated at certain point on the filtration surface to partially increase the amount of viruses to be loaded at the point and thus the viruses may be leaked from the point in a large capacity filtration under a high pressure condition. When the virus removal membrane 10 has a hollow fiber membrane shape, the amount of viruses captured on the virus capture portion is not ununiform as illustrated in FIG. 2, but preferably uniform as illustrated in FIG. 3, in the periphery direction.

Furthermore, in the virus removal membrane 10, the thickness of a portion where viruses are captured is preferably uniform in the virus capture portion. When the virus removal membrane 10 has the hollow fiber membrane shape, the thickness of the virus capture portion is preferably uniform in the periphery direction. The reason for this is because, when the thickness of the virus capture portion is uniform, the solution can be uniformly spread in the periphery direction to result in reduction in virus leakage.

The structure of the virus removal membrane 10 is preferably an asymmetric structure where a pore size is decreased and then increased, from the primary surface towards the secondary surface. In the cross section of the virus removal membrane 10, the virus capture portion includes a portion where the pore size of a pore is minimum.

The structure including a portion where the pore size of the pore is minimum is effective for an enhancement in virus removal property.

Here, it may be difficult to visually detect a virus captured by the virus removal membrane 10. On the contrary, a gold colloid does not allow light to transmit while it has a diameter comparable with a size of a virus, and therefore it is visually detected easily. Therefore, characteristics of the virus removal membrane 10 can be evaluated by, for example, filtering a gold colloid-containing solution by the virus removal membrane 10, and thereafter measuring the relative brightness of a gold colloid capture portion, where the gold colloids are captured by the virus removal membrane 10, in the cross section of the virus removal membrane 10.

With respect to the virus removal membrane 10 according to the embodiment, when a solution containing gold colloids having a diameter of 20 nm is applied through the primary surface 1 to the virus removal membrane 10 to allow the virus removal membrane 10 to capture the gold colloids for measurement of brightness in the cross section of the virus removal membrane 10, the value obtained by dividing the standard deviation of the value of the area of the spectrum of variation in the brightness by the average of the value of the area of the spectrum of variation in the brightness is 0.01 or more and 1.50 or less. The value expresses the variation coefficient of the amount of the gold colloids that are captured in the virus removal membrane 10, and a smaller value expresses higher uniformity of the amount of the gold colloids that are captured on the gold colloid capture portion in the virus removal membrane 10.

In the virus removal membrane 10 according to the embodiment, the value indicating the variation coefficient is 0.01 or more and 1.50 or less, 0.01 or more and 1.40 or less, 0.01 or more and 1.30 or less, 0.01 or more and 1.20 or less, 0.01 or more and 1.10 or less and 0.01 or more and 1.00 or less. The measurement limit of the variation coefficient is less than 0.01. A variation coefficient of more than 1.50 may cause the solution to be concentrated at at least certain one point in the periphery direction of the membrane to thereby result in virus leakage.

A variation coefficient of 0.01 or more and 1.50 or less can allow viruses to be uniformly captured on the virus capture portion of the membrane (in the periphery direction with respect to the hollow fiber membrane), and allow high virus removal performance to be maintained even in the case of an increase in the total amount of viruses to be loaded to the virus removal membrane (the amount of viruses to be spiked to a pharmaceutical protein, or the total amount thereof to be filtered off).

The variation coefficient is measured by, for example, the following method. A piece is cut out from the virus removal membrane applied to filtration of a gold colloid solution, and the brightness profile at each of a plurality of points in a part stained by the gold colloids in the cross section of the piece is measured by an optical microscope. A gold colloid absorbs light and therefore variation in the brightness depends on the amount of the gold colloids that are captured. Herein, a background noise may be, if necessary, removed from the brightness profile. Thereafter, a graph with the thickness represented on the horizontal axis and variation in the brightness represented on the vertical axis is created, and the area of the spectrum of variation in the brightness presented on the graph is calculated. Furthermore, the value obtained by dividing the standard deviation of the area of the spectrum of variation in the brightness at the plurality of points by the average of the area of the spectrum of variation in the brightness at the plurality of points is calculated as the value indicating the variation coefficient of the amount of the gold colloids that are captured on the gold colloid capture portion in the virus removal membrane 10.

The thickness of a portion, where gold colloids having a diameter of 20 nm or more and 30 nm or less are captured, in the cross section of the virus removal membrane 10 in a wet state is 10.0 μm or more and 30.0 μm or less, 10.0 μm or more and 25.0 μm or less, 10.0 μm or more and 22.0 μm or less, 10.0 μm or more and 20.0 μm or less, preferably 11.0 μm or more and 20.0 μm or less, more preferably 12.0 μm or more and 20.0 μm or less, further preferably 13.0 μm or more and 20.0 μm or less. When a thickness of the gold colloid capture portion is more than 30.0 μm, efficiency of filtration of not only a gold colloid-containing solution but also a virus-containing solution tends to be reduced. A thickness of less than 10 μm is not preferable because an increase in the total amount of viruses to be loaded to the virus removal membrane (the amount of viruses to be spiked to a pharmaceutical protein, or the total amount thereof to be filtered off) may result in virus leakage.

The thickness of the portion where the gold colloids having the diameter of 20 nm or more and 30 nm or less is captured is acquired by, for example, the following method. A piece is cut out from the virus removal membrane applied to filtration of each of respective solutions of gold colloids having diameters of 20 nm and 30 nm. The brightness profile at each of a plurality of points in a part stained by the gold colloids in the cross section of the piece is measured by an optical microscope. Herein, a first distance "a" from the primary surface 1 of the virus removal membrane 10 to a part of the gold colloid capture portion where is closest to the primary surface is measured in the thickness direction. In addition, a second distance "b" from the primary surface 1 of the virus removal membrane 10 to a part of the gold colloid capture portion where is closest to the secondary surface 2 is measured in the thickness direction.

Next, the value "A" (=a/c (expressed in percentage)) obtained by division of the first distance "a" by the thickness "c" of the wet virus removal membrane and expressed in percentage is calculated at each of the plurality of points, and the average of the value "A" at the plurality of points is calculated as a first attainment level. In addition, the value "B" (=b/c (expressed in percentage)) obtained by division of the second distance "b" by the thickness "c" of the wet virus removal membrane and expressed in percentage is calculated at each of the plurality of points, and the average of the value "B" at the plurality of points is calculated as a second attainment level.

Furthermore, as represented by the following expression (1), the value obtained by multiplication of the difference between the average "$B_{20}$" of the second attainment level in the virus removal membrane applied to capturing of the gold colloids having the diameter of 20 nm by filtration, and the average "$A_{30}$" of the first attainment level in the virus removal membrane applied to capturing of the gold colloids having the diameter of 30 nm by filtration, by the average "$C_{AVE}$" of the average "$C_{20}$" of the thickness of the wet virus removal membrane applied to capturing of the gold colloids having the diameter of 20 nm by filtration and the average "$C_{30}$" of the thickness of the wet virus removal membrane applied to capturing of the gold colloids having the diameter of 30 nm by filtration is calculated as the thickness "T" of the portion, where the gold colloids having the diameter of 20 nm or more and 30 nm or less are captured, in the cross section of the virus removal membrane 10 in flowing of the gold colloids having the diameter of 20 nm and the gold colloids having the diameter of 30 nm. The thickness "T" of the gold colloid capture portion is also expressed as the thickness "T" of the dense layer of the virus removal membrane.

$$T=(B_{20}-A_{30})\times C_{AVE} \qquad (1)$$

In the above method, the portion where the gold colloids having the diameter of 20 nm or more and 30 nm or less are captured is determined as the thickness of a region between the first attainment position in the virus removal membrane applied to capturing of the gold colloids having the diameter of 30 nm by filtration and the second attainment position in the virus removal membrane applied to capturing of the gold colloids having the diameter of 20 nm by filtration, and it is confirmed that the gold colloids having the diameter of 20 nm or more and 30 nm or less, except for the margin of error, are captured within the region.

When the solution containing the gold colloids having the diameter of 30 nm is filtered by the virus removal membrane 10, the portion where the gold colloids having the diameter of 30 nm are captured in the cross section of the virus removal membrane 10 in a wet state is located at a place corresponding to, for example, 15% or more and 60% or less, or 20% or more and 55% or less of the membrane thickness from the primary surface 1 in measurement with an optical microscope. In a membrane where gold colloids having a diameter of 30 nm are captured at a place corresponding to less than 15% of the membrane thickness from the primary surface, viruses and impurities are captured at a position closer to the primary surface of the membrane, and clogging may therefore more occur. In addition, in a membrane where gold colloids having a diameter of 30 nm are captured at a place corresponding to more than 60% of the membrane thickness from the primary surface, the intended viruses are captured at a position closer to the secondary surface of the membrane, and therefore the viruses cannot be sometimes captured. Herein, even when a small amount of the gold colloids having the diameter of 30 nm is captured in a region of less than 15% or more than 60% of the membrane thickness from the primary surface 1, a case where the absolute value of the spectrum of variation in the brightness, determined by subtracting the brightness profile measured from a constant (255) in observation with an optical microscope, is 10% or less relative to the maximum of the absolute value of the spectrum can be regarded as being within the margin of error with respect to gold colloid capture in the region, in terms of virus removal ability of the virus removal membrane. Accordingly, in such a case, the portion where the gold colloids having the diameter of 30 nm are captured can be regarded as being located at a place corresponding to 15% or more and 60% or less of the membrane thickness from the primary surface 1.

The portion where the gold colloids are captured may be continuously formed or intermittently formed in the thickness direction depending on the membrane structure in passing of the gold colloids from the primary surface towards secondary surface in the membrane thickness direction. In the virus removal membrane according to the embodiment, the portion where the gold colloids are captured is preferably continuously formed from the inside of the primary surface towards the inside of the secondary surface. When the portion where the gold colloids are captured is continuously formed in the passing direction without any discontinuity, clogging hardly occurs.

When the solution containing the gold colloids having the diameter of 20 nm is filtered by the virus removal membrane 10, a portion where the gold colloids having the diameter of 20 nm are captured in the cross section of the virus removal membrane 10 in a wet state is located at a place corresponding to, for example, 25% or more and 85% or less, or 30% or more and 80% or less of the membrane thickness from the primary surface 1 in measurement with an optical microscope. In a membrane where gold colloids having a diameter of 20 nm are captured at a place corresponding to less than 25% of the membrane thickness from the primary surface, viruses and impurities are captured at a position closer to the primary surface of the membrane, and clogging may therefore more occur. In addition, in a membrane where gold colloids having a diameter of 20 nm are captured at a place corresponding to more than 85% of the membrane thickness from the primary surface, the intended viruses are captured at a position closer to the secondary surface of the membrane, and therefore the viruses cannot be sometimes captured. Herein, even when the gold colloids are observed in the region of less than 25% or more than 85% of the membrane thickness from the primary surface 1 as in the case of the gold colloids having the diameter of 30 nm, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error. Herein, in the virus removal membrane according to the embodiment, the portion where the gold colloids having the diameter of 20 nm are captured is preferably continuously formed in the membrane thickness direction from the inside of the primary surface towards the inside of the secondary surface.

When a solution containing the gold colloids having the diameter of 15 nm is filtered by the virus removal membrane 10, a portion where the gold colloids having the diameter of 15 nm are captured in the cross section of the virus removal membrane 10 in a wet state is located at a place corresponding to, for example, 60% or more and 90% or less, preferably 60% or more and 89% or less, 60% or more and 88% or less, 60% or more and 87% or less of the membrane thickness from the primary surface 1 in measurement with an optical microscope. In particular, a value of 87% or less is preferable in terms of virus capture. Furthermore, a value of 86% or less is more preferable. In a membrane where gold colloids having a diameter of 15 nm are captured at a place corresponding to less than 60% of the membrane thickness from the primary surface, viruses and impurities are captured at a position closer to the primary surface of the membrane, and therefore clogging may more occur. In addition, in a membrane where gold colloids having a diameter of 15 nm are captured at a place corresponding to more than 90% of the membrane thickness from the primary surface, the intended viruses are captured at a position closer to the secondary surface of the membrane, and therefore the viruses cannot be sometimes captured. Herein, even when the gold colloids are observed in the region of less than 60% or more than 90% of the membrane thickness from the primary surface 1 as in the cases of respective gold colloids having diameters of 30 nm and 20 nm, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error. Herein, in the virus removal membrane according to the embodiment, the portion layer where the gold colloids having the diameter of 15 nm are captured is preferably continuously formed in the membrane thickness direction from the inside of the primary surface towards the inside of the secondary surface.

The capture position of each of respective gold colloids having diameters of 30 nm, 20 nm and 15 nm is consistently measured with respect to gold colloids captured by the membrane. Accordingly, gold colloids that are not captured by the membrane and that permeate through the membrane are not subjected to such measurement. In other words, a capture position of every gold colloid allowed to permeate through the membrane is not measured, but the capture position of gold colloids captured by the membrane, on the membrane, is measured.

When a solution containing the gold colloids having the diameter of 10 nm is filtered by the virus removal membrane 10, almost no gold colloids having the diameter of 10 nm are captured in the cross section of the virus removal membrane 10. This can be confirmed from the following: the spectrum of the brightness cannot be significantly detected in observation using an optical microscope (Biozero, BZ 8100, manufactured by Keyence Corporation). This can also be confirmed from a reduction in a logarithmic removal rate. Herein, no gold colloids having the diameter of 10 nm being captured indicates that useful proteins having a diameter of about 10 nm, such as IgG, can achieve high permeability.

The material of the virus removal membrane 10 includes cellulose. As such cellulose, regenerated cellulose, natural cellulose, cellulose acetate, and the like can be used. A method of producing regenerated cellulose includes a method (cuprammonium method) including preparing regenerated cellulose from a cuprammonium cellulose solution, and a method (saponification method) including saponifying cellulose acetate by an alkali to produce regenerated cellulose.

Figure 4:
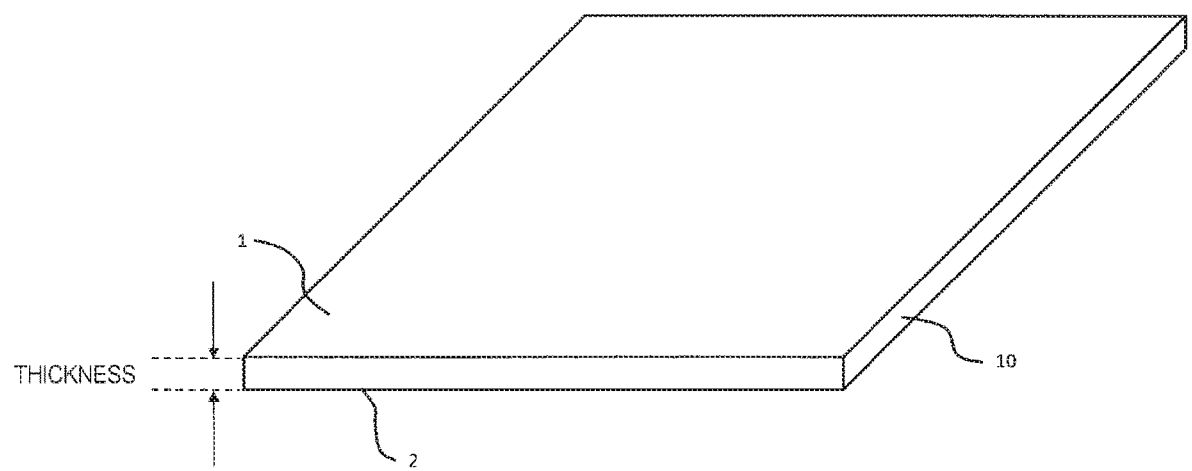
FIG. 4 is a schematic view of a virus removal membrane having a flat membrane shape, according to an embodiment of the present invention.

The virus removal membrane 10 has, for example, a hollow fiber membrane shape. Alternatively, the virus removal membrane 10 may have a flat membrane shape as illustrated in FIG. 4. The hollow fiber membrane, even though having a large membrane area, can be packed in a container to make a compact filter.

The thickness of the virus removal membrane 10 illustrated in FIG. 1 is, for example, 24 μm or more and 41 μm or less, preferably 24 μm or more and 40 μm or less, more preferably 24 μm or more and 35 μm or less, further more preferably 24 μm or more and 30 μm or less, in a dry state. A membrane thickness of less than 24 μm may result in a reduction in strength of the membrane to cause the membrane not to withstand the filtration pressure, and a thickness of more than 41 μm may result in a reduction in filtration rate.

The average pore size of the pore of the virus removal membrane 10 is, for example, 13 nm or more and 21 nm or less, preferably 13 nm or more and 20.5 nm or less, more preferably 13.5 nm or more and 20.5 nm or less. An average pore size of less than 13 nm may result in a reduction in filtration rate, and an average pore size of more than 21 nm may cause virus leakage to occur. The pore size of the pore is decreased and then increased from the primary surface towards the secondary surface in the cross section of the virus removal membrane 10. For example, the virus capture portion includes a portion where the pore size of the pore is minimum, in the cross section of the virus removal membrane 10.

The logarithmic removal rate (LRV: Logarithmic Reduction Value) of virus by the virus removal membrane 10 is preferably, for example, 4.00 or more because viruses are sufficiently removed by membrane filtration, and the logarithmic removal rate is more preferably 4.50 or more, 5.00 or more, or 6.00 or more. A logarithmic removal rate of virus of 6.00 or more is considered to allow viruses to be removed, resulting in almost no virus leakage.

The virus removal membrane 10 has a logarithmic removal rate (LRV) of gold colloid having a diameter of 30 nm, of, for example, 1.00 or more, preferably 1.20 or more. The virus removal membrane 10 has a logarithmic removal rate of gold colloid having a diameter of 20 nm, of, for example, 1.00 or more, preferably 1.20 or more. The virus removal membrane 10 has a logarithmic removal rate of gold colloid having a diameter of 15 nm, of, for example, 0.10 or more, preferably 0.15 or more, more preferably 0.20 or more. The virus removal membrane 10 has a logarithmic removal rate of gold colloid having a diameter of 10 nm, of, for example, less than 0.10.

For example, the gold colloid capture portion includes a portion where the pore size of the pore is minimum, in the cross section of the virus removal membrane 10.

The bubble point measured in the virus removal membrane 10 is, for example, 1.2 MPa or more and 1.8 MPa or less. The pure water permeation rate measured in the virus removal membrane 10 is 30 L/m$^2$/hrs/0.1 MPa, or more and 120 L/m$^2$/hrs/0.1 MPa, or less, 40 L/m$^2$/hrs/0.1 MPa, or more and 115 L/m$^2$/hrs/0.1 MPa, or less, or 50 L/m$^2$/hrs/0.1 MPa, or more and 110 L/m$^2$/hrs/0.1 MPa, or less.

The virus removal membrane according to the embodiment, having characteristics described above, is manufactured by, for example, a method described below. In production of the virus removal membrane in the form of the hollow fiber membrane, first, a cuprammonium cellulose solution in which cellulose is dissolved in a cuprammonium solution so that the cellulose concentration is, for example, about 7.0% by weight or more and about 8.0% by weight or less is prepared, and an inorganic salt is added thereto to provide a raw spinning solution. Herein, the inorganic salt may be added before cellulose is dissolved in a cuprammonium solution. As the inorganic salt, sulfates, sulfites, and carbonates of sodium, potassium, calcium, and magnesium can be used. Among them, sulfates and sulfites of sodium and potassium are preferable, and sodium sulfate and sodium sulfite are more preferable. The amount of the inorganic salt to be added is 0.02% by weight or more and 0.90% by weight or less, 0.03% by weight or more and 0.80% by weight or less, or 0.04% by weight or more and 0.70% by weight or less.

In addition, a solution that allows microphase separation to the cuprammonium cellulose solution to occur, the solution including at least one organic solvent having no hydroxyl group, having a solubility in an aqueous 28% by weight ammonia solution, of 10% by weight or more, and not swelling cellulose, is prepared as a coagulation liquid. Such microphase separation is described later. For example, the coagulation liquid includes acetone, ammonia and water. In production of the hollow fiber membrane, as described later, an internal coagulation liquid and an external coagulation liquid are prepared. In the internal coagulation liquid, for example, the acetone concentration is about 30% by weight or more and about 50% by weight or less, and the ammonia concentration is about 0.5% by weight or more and about 1.0% by weight or less. In the external coagulation liquid, for example, the acetone concentration is about 20% by weight or more and about 40% by weight or less, and the ammonia concentration is about 0% by weight or more and about 0.2% by weight or less.

Next, the raw spinning solution is discharged through an annular double spinneret at a constant rate of 1.5 cc/min or more and 8.0 cc/min or less, and at the same time, the internal coagulation liquid is discharged through a center spinning outlet provided on the center of the annular double spinneret. The raw spinning solution and the internal coagulation liquid discharged are immersed in the external coagulation liquid in a coagulation bath. Here, microphase separation occurs in the raw spinning solution by the action of the internal and external coagulation liquids. Such microphase separation means that a cellulose concentration phase is separated as particles having a diameter of 0.01 to several μm from a solvent or a cellulose dilution phase, and dispersed and stabilized. The microphase separation first occurs at the interface between the raw spinning solution, and the internal and external coagulation liquids, and also gradually occurs in the interior of the raw spinning solution. The particles formed by the microphase separation are formed into large particles, while colliding and coalescing being repeated. At the same time, the particles are gradually solidified by the action of the coagulation liquid, and are formed into a hollow fiber membrane having a polymer porous structure in which the particles are three-dimensionally linked. The hollow fiber membrane formed is wound up.

When the coagulation bath is formed by a narrow tube, the flow velocity of the raw spinning solution in the coagulation bath is, for example, 5 m/min or more and 20 m/min or less, 8 m/min or more and 15 m/min or less, or 9 m/min or more and 12 m/min or less. Herein, the flow velocity of the raw spinning solution in the coagulation bath is equal to the wind-up speed (spinning speed) of the hollow fiber membrane to be formed. The flow rate of the external coagulation liquid to be applied to the coagulation bath is, for example, 50 cc/min or more and 500 cc/min or less, 100 cc/min or more and 300 cc/min or less, or 130 cc/min or more and 200 cc/min or less. The flow velocity of the external coagulation liquid in the coagulation bath, determined by division of the flow rate of the external coagulation liquid by the cross-sectional area of the narrow tube forming the coagulation bath, is, for example, 1.8 m/min or more and 10.4 m/min or less, 3.2 m/min or more and 7.8 m/min or less, or 3.5 m/min or more and 5.4 m/min or less. Furthermore, the ratio of the flow velocity of the external coagulation liquid to the flow velocity of the raw spinning solution in the coagulation bath is, for example, 0.32 or more and 0.54 or less, or 0.33 or more and 0.53 or less. Herein, when the ratio of the flow velocity of the external coagulation liquid to the flow velocity of the raw spinning solution is in the above range, the respective absolute values of the flow velocity of the raw spinning solution and the flow velocity of the external coagulation liquid are arbitrary.

The hollow fiber membrane wound up is immersed in dilute sulfuric acid of 2% by weight or more and 10% by weight or less, and then washed with pure water. Thus, cellulose is regenerated. Furthermore, moisture in the hollow fiber membrane is replaced with an organic solvent. As the organic solvent, methanol, ethanol, acetone, and the like can be used. Thereafter, both ends of the hollow fiber membrane bundle are secured, and the hollow fiber membrane bundle is stretched by 1% to 8%, and thereafter dried at 30° C. or higher and 60° C. or lower under a reduced pressure of 5 kPa or less, to provide the virus removal membrane in the form of the hollow fiber membrane.

Conventionally, no inorganic salt has been added to a raw spinning solution. On the contrary, the present inventors have found for the first time that the inorganic salt can be added to the raw spinning solution to thereby change the diffusion speed of the particles formed by the cellulose concentration phase, affecting the progress speed of the microphase separation. Therefore, the membrane structure, for example, the degree of change (gradient) of each of the pore size from the surface to the inside of the virus removal membrane and the pore size in the membrane thickness direction can be controlled, and the thickness of the virus capture portion can be controlled to a proper thickness. In addition, the inorganic salt can be added to thereby stabilize the solubility of cellulose, allow microlayer separation to uniformly progress in the circumferential direction, and form a structure in which the amount of virus capture is uniform in the virus capture portion regardless of the place on the filtration surface.

Furthermore, the present inventors have also found that it is effective for making the virus capture portion and/or gold colloid capture portion of the virus removal membrane homogenous and fine to suppress the bath resistance in the coagulation bath in a coagulation process of a polymer porous membrane. The bath resistance in the coagulation bath can be suppressed to thereby suppress breakage of the membrane structure due to stretching, forming a uniform membrane structure in the circumferential direction of the membrane. The bath resistance in the coagulation bath can be suppressed by setting a proper relationship between the flow velocity of the raw spinning solution and the flow velocity of the coagulation liquid. Specifically, the ratio of the flow velocity of the coagulation liquid to the flow velocity of the raw spinning solution is set within the above range to thereby suppress the bath resistance in the coagulation bath.

As described above, the microphase separation can be controlled and the bath resistance in the coagulation bath can be suppressed in a manufacturing process, to thereby allow the virus removal membrane in the form of the hollow fiber membrane, having the high virus removal property, to be manufactured.

In addition, the virus removal membrane in the form of the flat membrane is manufactured by, for example, the following method. An inorganic salt is added to a cuprammonium cellulose solution and mixed therewith, to provide a membrane formation solution. Subsequently, the membrane formation solution is subjected to filtration and degassing treatments. The type of the inorganic salt to be used is the same as described above.

Next, the membrane formation solution is cast and spread on a support traveling in a coagulation bath, and coagulated. The movement speed of the support is set to be about 1.0 to 10.0 m/min. A flat membrane formed is subjected to a regeneration treatment with an acid, allowed to pass through an additional water bath and drawn, and thereafter dried by use of a drier. In order to make the virus capture portion and/or gold colloid capture portion of the virus removal membrane in the form of the flat membrane, to be manufactured, homogeneous and fine, the casting speed and the movement speed of the coagulation liquid is set to be in a proper relationship. Specifically, the ratio of the movement speed of the coagulation liquid to the movement speed of the support is set to be in a certain range.

The hollow fiber and flat membrane virus removal membranes manufactured by the above methods can be used for making a filter in which a primary space close to the inlet of a liquid to be filtered and a secondary space close to the outlet of a filtrate are partitioned by a membrane.

Although the present invention has been described above with reference to embodiments, it should not be understood that the present invention is limited by the description and the drawings constituting a part of the disclosure. Various alternative embodiments, examples and operation techniques would be apparent to one skilled in the art, based on the disclosure. It should be understood that the present invention encompasses various embodiments and the like not described here.

EXAMPLES

Manufacturing Virus Removal Membrane

A cotton linter (average molecular weight: $1.44 \times 10^5$) and sodium sulfate (manufactured by Kishida Chemical Co., Ltd.) were dissolved in a cuprammonium solution prepared by a known method, and filtered and defoamed to provide a raw spinning solution in which the cellulose concentration, and the concentration of sodium sulfate as an inorganic salt were as described in FIG. 5 and FIG. 6, the ammonia concentration was 4.4% by weight, and the copper concentration was 2.7% by weight. Next, the raw spinning solution was discharged through the outer spinning outlet of the annular double spinneret at a rate of 3.0 cc/min or 3.65 cc/min, and at the same time, an internal coagulation liquid including acetone/ammonia/water in a weight ratio represented in FIG. 5 and FIG. 6 was discharged through the center spinning outlet of the annular double spinneret at a rate of 1.8 cc/min.

The raw spinning solution and the internal coagulation liquid discharged through the annular double spinneret were introduced in a coagulation bath filled with the external coagulation liquid including acetone/ammonia/water in a weight ratio represented in FIG. 5 and FIG. 6, to form a hollow fiber membrane, and the hollow fiber membrane was wound up at a wind-up speed (spinning speed) of 10 m/min. As the coagulation bath, a U-shaped funnel narrow tube having a diameter of 7 mm, described in Japanese Patent Laid-Open No. 4-371221, was used. The average flow velocity of the external coagulation liquid in the funnel narrow tube was as represented in FIG. 5 and FIG. 6. In addition, the ratio of the average flow velocity of the external coagulation liquid to the wind-up speed (spinning speed) was as represented in FIG. 5 and FIG. 6.

The hollow fiber membrane was wound up in water at 30° C. After the hollow fiber membrane was wound up for 60 minutes, the hollow fiber membrane wound up was immersed in another water at 30° C. for 60 minutes. Thereafter, cellulose of the hollow fiber membrane was regenerated by an aqueous 5% by weight sulfuric acid solution, and further washed with water. The moisture in the resulting hollow fiber membrane bundle was replaced with methanol in each of Examples 1 to 4 as well as Comparative Examples 1, 2 and 4, and ethanol in each of Examples 5 to 9, and thereafter subjected to vacuum drying in conditions of 50° C. and 3 kPa while both ends of the bundle were secured and stretched by 5.0%. The hollow fiber membrane obtained by the foregoing method was defined as a virus removal membrane according to each Example or Comparative Example. No membrane itself, however, could be manufactured in conditions according to Comparative Example 3 and Comparative Example 5 represented in FIG. 5 and FIG. 6. The inner diameter, the membrane thickness, the average pore size, the bubble point, and the pure water permeation rate before sterilization of the resulting virus removal membrane were as represented in FIG. 5 and FIG. 6.

(Evaluation of Virus Removal Membrane Using Gold Colloids)

(1) Preparation of Gold Colloid Solution

Respective solutions including gold colloids having particle sizes of 10, 15, 20, and 30 nm (manufactured by Cytodiagnostics Inc.) were purchased. Next, each of the gold colloid solutions was diluted with distilled water for injection, polyoxyethylene-naphthyl ether (1.59% by vol), and poly(sodium 4-styrenesulfonate) (0.20% by vol) so that the absorbance at the maximum absorption wavelength of the gold colloids of each of the gold colloid solutions, measured by an ultraviolet-visible spectrophotometer UVmini-1240 (manufactured by Shimadzu Corporation), was 0.25.

(2) Filtration of Gold Colloid Solution 40 mL of each of the gold colloid solutions prepared was filtered under a pressure of 78.4 kPa by the virus removal membrane manufactured in each of Examples and Comparative Examples. The filtration surface area of the virus removal membrane was 0.001 m².

(3) Measurement of Removal Rate of Gold Colloids by Virus Removal Membrane

With respect to each of the gold colloid solutions, the absorbance "A" of the gold colloid solution before filtration and the absorbance "B" of the filtrate, at the maximum absorption wavelength of gold colloids, were measured using an ultraviolet-visible spectrophotometer UVmini-1240 (manufactured by Shimadzu Corporation), and the logarithmic removal rate (LRV) of gold colloid by the virus removal membrane according to each of Examples and Comparative Examples, given by the following expression (2), was calculated. The results are represented in FIG. 7 and FIG. 8.

$$LRV = \log_{10}(A/B) \qquad (2)$$

(4) Measurement of Uniformity of Gold Colloid Capture Portion

A piece (thickness: 8 μm) was cut out from the virus removal membrane according to each of Examples and Comparative Examples after filtration of each of the gold colloid solutions, and the brightness profile at each of 16 points stained by the gold colloids in the cross section of the piece was measured by an optical microscope (Biozero, BZ8100, manufactured by Keyence Corporation). Next, the brightness profile measured was subtracted from a constant (255). Thereafter, a graph with the membrane thickness (percentage) represented on the horizontal axis and variation in the brightness represented on the vertical axis was created, and the area of the spectrum of variation in the brightness presented on the graph was calculated. Furthermore, the value obtained by dividing the standard deviation of the area of the spectrum of variation in the brightness at 16 points by the average of the area of the spectrum of variation in the brightness at 16 points was calculated as the value indicating the variation coefficient of the amount of captured gold colloids, on the gold colloid capture portion in the virus removal membrane according to each of Examples and Comparative Examples. The results in flowing of only the gold colloids having the diameter of 20 nm are represented in FIG. 7 and FIG. 8. The virus removal membrane according to each Example tended to be low in variation coefficient as compared with the virus removal membrane according to each Comparative Example. Accordingly, it was indicated that uniformity of the amount of captured gold colloids on the gold colloid capture portion of the virus removal membrane according to each Example was high. In addition, among Examples, as the amount of added sodium sulfate was larger, and the ratio of the average flow velocity of the external coagulation liquid to the spinning speed was larger, uniformity of the amount of captured gold colloids on the gold colloid capture portion tended to be higher.

(5) Measurement of Thickness of Gold Colloid Capture Portion

A piece (thickness: 8 μm) was cut out from the virus removal membrane in a wet state with which the respective solutions of gold colloids having diameters of 20 and 30 nm were filtered. The brightness profile at each of 16 points stained by the gold colloids in the cross section of the piece in a wet state was measured by an optical microscope (Biozero, BZ8100, manufactured by Keyence Corporation). Here, a first distance "a" from the primary surface of the virus removal membrane to a part where the gold colloids were captured and where is closest to the primary surface was measured in the thickness direction. In addition, a second distance "b" from the primary surface of the virus removal membrane to a part where the gold colloids were captured and where is closest to the secondary surface was measured in the thickness direction.

Next, the value "A" (=a/c (expressed in percentage)) obtained by division of the first distance "a" by the thickness "c" of the virus removal membrane in a wet state and expressed in percentage was calculated at each of 16 points, and the average of the value "A" at 16 points was calculated as the first attainment level. In addition, the value "B" (=b/c (expressed in percentage)) obtained by division of the second distance "b" by the thickness "c" of the virus removal membrane in a wet state and expressed in percentage was calculated at each of 16 points, and the average of the value "B" at 16 points was calculated as the second attainment level.

Furthermore, as represented by the following expression (3), the value obtained by multiplication of the difference between the average "$B_{20}$" of the second attainment level in the virus removal membrane applied to capturing of the gold colloids having the diameter of 20 nm by filtration, and the average "$A_{30}$" of the first attainment level in the virus removal membrane applied to capturing of the gold colloids having the diameter of 30 nm by filtration, by the average "$C_{AVE}$" of the average "$C_{20}$" of the thickness of the virus removal membrane in a wet state applied to capturing of the gold colloids having the diameter of 20 nm by filtration and the average "$C_{30}$" of the thickness of the virus removal membrane in a wet state applied to capturing of the gold colloids having the diameter of 30 nm by filtration was calculated as the thickness "T" of the gold colloid capture portion of the virus removal membrane. The thickness "T" of the gold colloid capture portion is also expressed as the thickness "T" of a dense layer of the virus removal membrane. The results are represented in FIG. 7 and FIG. 8. The virus removal membrane according to each Example tended to have a large thickness "T" of the dense layer, which was in the range of 20 μm or less, as compared with the virus removal membrane according to each Comparative Example. In addition, among Examples, as the amount of added sodium sulfate was larger, and the ratio of the average flow velocity of the external coagulation liquid to the spinning speed was larger, the thickness of the fine layer tended to be increased.

$$T = (B_{20} - A_{30}) \times C_{AVE} \quad (3)$$

In the above method, at least two virus removal membranes: the virus removal membrane applied to capturing of the gold colloids having the diameter of 20 nm by filtration and the virus removal membrane applied to capturing of the gold colloids having the diameter of 30 nm by filtration; were used to measure the thickness of the dense layer. Only one virus removal membrane, however, can also be used to measure the thickness of the dense layer. In this case, one virus removal membrane was used to filter a gold colloid solution including gold colloids having both diameters of 20 nm and 30 nm. Alternatively, one virus removal membrane was used to filter a gold colloid solution with a diameter of 20 nm and then filter a gold colloid solution with a diameter of 30 nm.

Thereafter, a piece was cut out from the virus removal membrane with which each of the gold colloid solutions with diameters of 20 nm and 30 nm was filtered, and the brightness profile at each of 16 points stained by the gold colloids in the cross section of the piece were measured by an optical microscope (Biozero, BZ8100, manufactured by Keyence Corporation). Herein, a first distance "$a_1$" from the primary surface of the virus removal membrane to a part of the gold colloid capture portion where is closest to the primary surface was measured in the thickness direction. In addition, a second distance "$b_1$" from the primary surface of the virus removal membrane to a part of the gold colloid capture portion where is closest to the secondary surface was measured in the thickness direction.

Next, the value "$A_1$" (=$a_1/c_1$ (expressed in percentage)) obtained by division of the first distance "$a_1$" by the thickness "c" of the wet virus removal membrane and expressed in percentage was calculated at each of 16 points, and the average of the value "$A_1$" at 16 points was calculated as the first attainment level. In addition, the value "$B_1$" (=$b_1/c_1$ (expressed in percentage)) obtained by division of the second distance "$b_1$" by the thickness "c" of the wet virus removal membrane and expressed in percentage was calculated at each of 16 points, and the average of the value "$B_1$" at 16 points was calculated as the second attainment level.

Furthermore, as represented by the following expression (4), the value obtained by multiplication of the difference between the average "$B_1$" of the second attainment level in the virus removal membrane and the average "$A_1$" of the first attainment level in the virus removal membrane, by the average "C" of the thickness of the wet virus removal membrane was calculated as the thickness "T" of the gold colloid capture portion of the virus removal membrane. It was confirmed that no large difference occurred between the thickness "T" calculated by the expression (3) and the thickness "T" calculated by the expression (4).

$$T = (B_1 - A_1) \times C \quad (4)$$

(6) Measurement of Particle Size Dependence Property of Gold Colloid Capture Portion of Virus Removal Membrane A piece (thickness: 8 μm) was cut out from the virus removal membrane with which the respective gold colloid solutions with diameters of 15 nm, 20 nm and 30 nm were filtered. The brightness profile at each of 16 points stained by the gold colloids in the cross section of the piece was measured by an optical microscope (Biozero, BZ8100, manufactured by Keyence Corporation). Here, a first distance "a" from the primary surface of the virus removal membrane to a part where the gold colloids were captured and where is closest to the primary surface was measured in the thickness direction. In addition, a second distance "b" from the primary surface of the virus removal membrane to a part where the gold colloids were captured and where is closest to the secondary surface was measured in the thickness direction.

Next, the value "A" (%) obtained by division of the first distance "a" by the thickness "c" of the wet virus removal membrane and expressed in percentage was calculated at each of 16 points, and the average of the value "A" (%) at 16 points was calculated as the first attainment level. In addition, the value "B" (%) obtained by division of the second distance "b" by the thickness "c" of the wet virus removal membrane and expressed in percentage was calculated at each of 16 points, and the average of the value "B" (%) at 16 points was calculated as the second attainment level. The average of the first attainment level and the average of the second attainment level with respect to each of respective gold colloids having diameters of 15 nm, 20 nm and 30 nm are represented in FIG. 7 and FIG. 8. In FIG. 7 and FIG. 8, numerical values on the left each represent the average of the first attainment level, and numerical values on the right each represent the average of the second attainment level. The capture position of each of respective gold colloids having diameters of 30 nm, 20 nm and 15 nm was consistently measured with respect to gold colloids captured by the membrane, and gold colloids not captured by the membrane was not subjected to such measurement.

(Virus Removal Ability of Virus Removal Membrane)

(1) Preparation of Virus-Containing Protein Solution

A polyclonal antibody (human IgG) (Venoglobulin-IH, manufactured by Benesis Corporation) was used to provide an antibody solution that was diluted with water for injection (Otsuka Pharmaceutical Co., Ltd.) so as to have an antibody concentration of 1 mg/mL. The salt concentration was adjusted to 0.1 mol/L by use of an aqueous 1 mol/L NaCl solution. Furthermore, the hydrogen-ion exponent (pH) was adjusted to 4.0 by use of 0.1 mol/L HCl or 0.1 mol/L NaOH, to provide a protein solution. To the resulting protein solution was added porcine parvovirus (PPV; Japanese Association of Veterinary Biologics) in a concentration of 1.0% by vol, and well stirred to provide a virus-containing protein solution.

(2) Filtration of Virus-Containing Protein Solution

The virus removal membrane manufactured, having a membrane area of 0.001 m$^2$, was used at a filtration pressure of 78.4 kPa to perform dead-end filtration of the virus-containing protein solution until the amount of filtration reached 75 L/m$^2$. The filtration pressure was measured by a pressure gauge disposed close to a feed solution vessel. Next, 10-fold, 10$^2$-fold, 10$^3$-fold, 10$^4$-fold and 10$^5$-fold diluted solutions of the filtrate of the virus-containing protein solution, with 3% by vol FBS/D-MEM, were prepared. In addition, 10$^2$-fold, 10$^3$-fold, 10$^4$-fold, 10$^5$-fold, 10$^6$-fold and 10$^7$-fold diluted solutions of the virus-containing protein solution not filtered (virus-containing protein solution) which were taken immediately before filtration, with 3% by vol FBS/D-MEM, were also prepared.

(3) Measurement of Virus Removal Rate

Prepared was PK-13 cell (ATCC No. CRL-6489) obtained from American Type Culture Collection (ATCC) and cultured. In addition, prepared was a mixed liquid of 3% by vol of bovine serum (manufactured by Upstate) heated in a water bath at 56° C. for 30 minutes and inactivated, and D-MEM (manufactured by Invitrogen Corporation, high glucose) containing 1% by vol of penicillin/streptomycin (+10000 Units/mL penicillin, +10000 µg/mL streptomycin, manufactured by Invitrogen Corporation). Hereinafter, the mixed liquid is referred to as "3% by vol FBS/D-MEM". Next, the PK-13 cell was diluted with 3% by vol FBS/D-MEM to prepare a diluted cell suspension having a cell concentration of 2.0×10$^5$ (cells/mL). Next, ten 96-well round-bottom cell culture plates (manufactured by Falcon Corporation) were prepared, and the diluted cell suspension was dispensed to all wells by 100 µL.

Each of the filtrate of the virus-containing protein solution, 10-fold, 10$^2$-fold, 10$^3$-fold, 10$^4$-fold and 10$^5$-fold diluted solutions of the filtrate, and 10$^2$-fold, 10$^3$-fold, 10$^4$-fold, 10$^5$-fold, 10$^6$-fold and 10$^7$-fold diluted solutions of the virus-containing protein solution not filtered was dispensed to every eight wells of each of the cell culture plates, to which the diluted cell suspension was dispensed, by 100 µL. Thereafter, each of the cell culture plates was placed in an incubator at 37° C. in a 5% carbon dioxide atmosphere, and the cell was cultured for 10 days.

The cell cultured for 10 days was subjected to 50% tissue culture infectious dose (TCID50) measurement by use of the erythrocyte adsorption method (see Experimental Study of Viruses, General, edited by National Institute of Infectious Diseases, p. 173) described below. First, preserved chicken blood (manufactured by Nippon Bio-Test Laboratories Inc.) was diluted 5-fold with PBS (−) (manufactured by Nissui Pharmaceutical Co., Ltd.; prepared by the method described in the instruction attached to the product) and then centrifuged at 2500 rpm at 4° C. for 5 minutes to precipitate erythrocytes. Thereafter, the supernatant was removed by aspiration, and the resulting erythrocyte-containing precipitate was diluted again 200-fold with the PBS (−).

Next, the PBS (−) diluted solution of the erythrocyte precipitate was dispensed by 100 µL to all wells of the cell culture plates, and left to still stand for two hours. Thereafter, the presence of the adsorption of erythrocytes to the surface of the cellular tissue cultured was visually confirmed, and a well where the adsorption was confirmed was counted as a well with viral infection and a well where the adsorption was not confirmed was counted as a well without viral infection. Furthermore, the degree of viral infection was confirmed every well, to which each of the filtrate of the virus-containing protein solution and the diluted solutions of the filtrate, and the diluted solutions of the virus-containing protein solution not filtered was dispensed, the log$_{10}$ (TCID$_{50}$/mL) was calculated as an infectivity titer according to the Reed-Muench method (see Experimental Study of Viruses, General, edited by National Institute of Infectious Diseases, p. 479-480), and the logarithmic removal rate (LRV) of virus was calculated using the following expression (5). The results are represented in FIG. 7 and FIG. 8. In comparison with the virus removal membrane according to each Comparative Example, the virus removal membrane according to each Example tended to be high in virus removal rate. In addition, among Examples, as the amount of added sodium sulfate was larger, and the ratio of the average flow velocity of the external coagulation liquid to the spinning speed was larger, the virus removal rate tended to be higher.

$$LRV=\log_{10}(C_0/C_F) \quad (5)$$

In the expression, $C_0$ represents the infectivity titer of the virus-containing protein solution not filtered (virus-containing protein solution) before filtration by the virus removal membrane, and $C_F$ represents the infectivity titer of the filtrate after filtration by the virus removal membrane.

(4) Measurement Method of Bubble Point (Measurement Method Described in International Publication No. WO 2001/014047)

When a membrane is wetted by a liquid having a surface tension γ (N/m) and thereafter pressure is gradually applied to the membrane by a gas, air bubbles are continuously generated from the membrane surface at a certain pressure, and the gas pressure here is measured. The gas pressure here is referred to as the bubble point (MPa).

In any known measurement method, the pressure at which generation of continuous air bubbles is visually confirmed is defined as the bubble point. Such a determination method, however, causes an error to easily occur because the amount of air bubbles to be generated is small in the case of a small membrane area and air bubbles may be thus overlooked, and air bubbles (not air bubbles generated by an interfacial fracture phenomenon) attached on the membrane surface before pressurizing, which are left from the membrane surface, may be mistaken as air bubbles by an interfacial fracture phenomenon.

In the present Example, in order to provide a smaller measurement error, the pressure (MPa) at which air bubbles were generated at a quantitative rate of 3.0 mL/min per square centimeter of the membrane area was defined as the bubble point. In addition, perfluorocarbon having a surface tension of 0.012 (N/m) was used as a wet liquid and nitrogen was used as a pressurizing gas.

(5) Measurement Method of Inner Diameter and Membrane Thickness (Dry Hollow Fiber)

In the present Example, the cross-sectional slice of the dry hollow fiber was observed by a projector (V-12B, manufactured by Nikon Corporation), the inner diameters at 2 points and the membrane thicknesses 4 points in the perpendicular direction and the horizontal direction every one hollow fiber cross section were measured, and the respective averages thereof were defined as the measurement values of the inner diameter and the membrane thickness.

(6) Measurement Method of Membrane Thickness (Wet Hollow Fiber)

When the hollow fiber membrane thickness in a wet state was measured in the present Example, the wet hollow fiber in capturing of gold colloids with diameters of 30 nm, 20 nm and 15 nm by filtration (40 L/m$^2$) was subjected to measurement by use of an optical microscope (Biozero, BZ8100, manufactured by Keyence Corporation).

(7) Measurement Method of Average Pore Size (Measurement Method Described in Japanese Patent No. 2707274)

In the present Example, the porosity "Pr" was calculated by the following method. The apparent density ρa of the hollow fiber was determined from measurements of the membrane thickness, the area and the weight, and the porosity was determined by expression (6).

$$\rho a = Wd/Vw = 4Wd/\pi l(Do^2 - Di^2)$$

$$Pr(\%) = (1 - \rho a/\rho p) \times 100 \quad (6)$$

In the expression, ρa represents the apparent density (g/cm$^3$) of the hollow fiber, Wd represents the bone-dry weight (g) of the hollow fiber, Vw represents the apparent volume (cm$^3$) of the hollow fiber, l represents the length (cm) of the hollow fiber, Do represents the outer diameter (cm) of the hollow fiber, Di represents the inner diameter (cm) of the hollow fiber, and ρp represents the density (g/cm$^3$) of cellulose.

The average pore size was calculated by the following method. Ten fibers were bundled to prepare a module so that the effective length was 16 cm. One end of the module was closed, a pressure of 200 mmHg was applied to other end thereof, and water was allowed to pass at 37° C. The amount of water coming out through the membrane was measured as the amount of water permeation.

In advance, the inner diameter and the membrane thickness were measured in a dry state. The membrane area was calculated from such values.

The average pore size (nm) was calculated by expression (7).

$$2r = 2 \times 10^3 \times \sqrt{(V^*d^*\mu/P^*A^*Pr)} \quad (7)$$

In the expression, 2r represents the average pore size (nm), V represents the amount of water permeation (mL/min), d represents the membrane thickness (μm), μ represents the viscosity (cp) of water, P represents the difference in pressure (mmHg), A represents the membrane area (cm$^2$), and Pr represents the porosity (%).

(8) Measurement Method of Average Molecular Weight

In the present Example, measurement was conducted by the same method as the method described in Japanese Patent Publication No. 59-204912.

(9) Measurement Method of Pure Water Permeation Rate Before Sterilization

The pure water permeation rate was obtained by filling both surfaces of the membrane: the primary surface for liquid feeding and the secondary surface for filtrate discharge; with pure water, thereafter filtering pure water at a temperature of 37° C. at a differential pressure in the membrane of 35 kPa, and converting the amount of permeation of pure water coming out from the primary surface towards the secondary surface to the unit (L/hrs/0.1 MPa per square meter of the dry hollow fiber membrane area). Pure water refers to water purified by ultrafiltration.

REFERENCE SIGNS LIST 1 primary surface
2 secondary surface
10 virus removal membrane

The invention claimed is:

1. A virus removal membrane for removing viruses from a protein-containing solution, the virus removal membrane comprising:

a primary surface configured to have the protein-containing solution applied thereto, and a secondary surface configured to allow a liquid that permeates through a thickness of the virus removal membrane to flow therefrom, wherein, a body of the virus removal membrane is configured such that, i) a value obtained by dividing a standard deviation of a value of an area of a spectrum of variation in the brightness by an average of the value of the area of the spectrum of variation in the brightness is 0.01 or more and 1.50 or less, wherein the brightness is measured for a cross section of the virus removal membrane after 40 mL of a solution containing gold colloids having a diameter of 20 nm is applied to a filtration area of 0.001 m$^2$ of the primary surface, filtered under a pressure of 78.4 kPa, and penetrates into the body of the virus removal membrane to allow the virus removal membrane to capture the gold colloids for measurement of brightness; and ii) a thickness of a portion where gold colloids having a diameter of 20 nm or more and 30 nm or less are captured in the cross section of the virus removal membrane in a wet state is 13.0 μm or more and 20.0 μm or less, wherein the thickness is measured after 40 mL of a solution containing gold colloids having a diameter of 20 nm or more and 30 nm or less is applied to the filtration area of 0.001 m$^2$ of the primary surface, filtered under the pressure of 78.4 kPa, and penetrates into the body of the virus removal membrane, wherein the body of the virus removal membrane is configured such that a portion where gold colloids having a diameter of 30 nm are captured is located at a place corresponding to 15% or more and 60% or less of a thickness of the virus removal membrane from the primary surface in the cross section of the virus removal membrane in a wet state after 40 mL of a solution containing the gold colloids having a diameter of 30 nm is applied to the filtration area of 0.001 m² of the primary surface, filtered under the pressure of 78.4 kPa, and penetrates into the body of the virus removal membrane, a portion where gold colloids having a diameter of 20 nm are captured is located at a place corresponding to 25% or more and 85% or less of the membrane thickness from the primary surface in the cross section of the virus removal membrane in a wet state after 40 mL of a solution containing the gold colloids having a diameter of 20 nm is applied to the filtration area of 0.001 m² of the primary surface, filtered under the pressure of 78.4 kPa, and penetrates into the body of the virus removal membrane, and a portion where gold colloids having a diameter of 15 nm are captured is located at a place corresponding to 60% or more and 100% or less of the membrane thickness from the primary surface in the cross section of the virus removal membrane in a wet state after 40 mL of a solution containing the gold colloids having a diameter of 15 nm is applied to the filtration area of 0.001 m² of the primary surface, filtered under the pressure of 78.4 kPa, and penetrates into the body of the virus removal membrane, wherein each of the solutions containing gold colloids are diluted with distilled water for injection, 1.59% by volume of polyoxyethylene-naphthyl ether, and 0.20% by volume of poly(sodium 4-styrenesulfonate) so that the absorbance at the maximum absorption wavelength of the gold colloids of the solution is 0.25 measured by an ultraviolet-visible spectrophotometer, and the virus removal membrane is formed of cellulose.

2. The virus removal membrane according to claim 1, wherein the body of the virus removal membrane is configured such that, when 40 mL of a solution containing gold colloids having a diameter of 10 nm is applied to the filtration area of 0.001 m² of the primary surface, filtered under the pressure of 78.4 kPa, and penetrates into the body of the virus removal membrane, gold colloids having a diameter of 10 nm is not captured, wherein the solution containing gold colloids having a diameter of 10 nm is diluted with distilled water for injection, 1.59% by volume of polyoxyethylene-naphthyl ether, and 0.20% by volume of poly(sodium 4-styrenesulfonate) so that the absorbance at the maximum absorption wavelength of the gold colloids of the solution is 0.25 measured by an ultraviolet-visible spectrophotometer.

3. The virus removal membrane according to claim 1, wherein
a logarithmic removal rate of gold colloid having a diameter of 30 nm is 1.00 or more,
a logarithmic removal rate of gold colloid having a diameter of 20 nm is 1.00 or more,
a logarithmic removal rate of gold colloid having a diameter of 15 nm is 0.10 or more, and
a logarithmic removal rate of gold colloid having a diameter of 10 nm is less than 0.10.

4. The virus removal membrane according to claim 1, wherein an average pore size is 13 nm or more and 21 nm or less.

5. The virus removal membrane according to claim 1, wherein a pore size is decreased and then increased, from the primary surface towards the secondary surface in the cross section of the virus removal membrane.

6. The virus removal membrane according to claim 5, wherein the portion where the gold colloids are captured includes a portion where the pore size is minimum.

7. The virus removal membrane according to claim 1, wherein a thickness of the membrane is 24 μm or more and 41 μm or less in a dry state.

8. The virus removal membrane according to claim 1, wherein a bubble point is 1.2 MPa or more and 1.8 MPa or less.

9. The virus removal membrane according to claim 1, wherein a pure water permeation rate is 30 L/m²/hrs/0.1 MPa, or more and 120 L/m²/hrs/0.1 MPa, or less.

10. The virus removal membrane according to claim 1, which is a hollow fiber membrane.

11. The virus removal membrane according to claim 1, wherein the value obtained by dividing a standard deviation of a value of an area of a spectrum of variation in the brightness by an average the value of an area of the spectrum of variation in the brightness is 0.01 or more and 1.20 or less.

12. The virus removal membrane according to claim 1, wherein the body of the virus removal membrane is manufactured with an average flow velocity of an external coagulation liquid at funnel/spinning speed being 0.32 or more.

13. The virus removal membrane according to claim 1, wherein the body of the virus removal membrane is a hollow fiber membrane having a uniform structure in the circumferential direction.

* * * * *

UNITED STATES PATENT AND TRADEMARK OFFICE
CERTIFICATE OF CORRECTION

PATENT NO. : 10,675,593 B2
APPLICATION NO. : 15/302278
DATED : June 9, 2020
INVENTOR(S) : R. Hamamoto et al.

It is certified that error appears in the above-identified patent and that said Letters Patent is hereby corrected as shown below:

In the Claims

Column 22, Line 37 (Claim 11, Line 4) please change "average the" to -- average of the --

Signed and Sealed this
Nineteenth Day of January, 2021

Andrei Iancu
*Director of the United States Patent and Trademark Office*